United States Patent [19]

Kriloff

[11] Plant 5,165

[45] Dec. 27, 1983

[54] ROSE PLANT CV. KRICARLO

[75] Inventor: Michel Kriloff, Antibes, France

[73] Assignee: Armstrong Nurseries, Inc., Ontario, Calif.

[21] Appl. No.: 409,902

[22] Filed: Aug. 20, 1982

[51] Int. Cl.[3] ..... A01H 5/00

[52] U.S. Cl. ..... Plt./18

[58] Field of Search ..... Plt./18

*Primary Examiner*—Robert E. Bagwill

*Attorney, Agent, or Firm*—Synnestvedt & Lechner

[57] ABSTRACT

A new variety of rose plant of the hybrid tea class, being a bushy seedling, particularly adapted for garden decoration; its long elegant pointed buds that open slowly with a distinctively classical spiraled form; its flowers are borne mostly one-to-a-stem on long strong stems which are suitable for cutting; its extremely long vase-life as a cut rose; its unique warm orange-pink coloration that holds well throughout the life of the flower; its extremely vigorous bush is easy-to-grow and produces a profusion of flowers nearly continually throughout the growing season, making a very attractive garden specimen; its consistently fine performance in a wide variety of climatic conditions; and its abundant deep green foliage attractively clothes the entire plant.

1 Drawing Figure

1

This invention relates to a new variety of hybrid tea rose. The plant is a seedling of the bushy outdoor type, cultivated for garden decoration. Its hardiness has not as yet been tested. It was first propagated in Antibes, France, but the plant described herein was one derived from budwood of that propagation, and was grown in Ontario, Calif. References to the growth and behavior of the plant pertain to plants raised in Southern California.

The new variety was bred by Michel Kriloff in Antibes, France, having as its seed parent "Micaela", and, as its pollen parent, an undisseminated seedling of "Queen Elizabeth×Romantica". It holds its distinguishing characteristics through succeeding propagations by budding.

This new rose cultivar is unique and distinguishable from existing rose cultivars by the following combination of characteristics: its long elegant pointed buds open slowly with a distinctively classical spiraled form; its flowers are borne mostly one-to-a-stem on long strong stems which are suitable for cutting; its extremely long vase-life as a cut rose; its unique warm orange-pink coloration that holds well throughout the life of the flower; its extremely vigorous bush is easy-to-grow and produces a profusion of flowers nearly continually throughout the growing season, making a very attractive garden specimen; its consistently fine performance in a wide variety of climatic conditions; and its abundant deep green foliage attractively clothes the entire plant.

This new rose cultivar may be distinguished from its seed parent, Micaela, by the following combination of characteristics.

Whereas Micaela produces flowers of a relatively uniform orange-red coloration, the new rose bears flowers of a relatively uniform coral pink coloration essentially as described and illustrated herein.

Micaela bears flower buds that are short and flat-topped whereas the new cultivar bears flower buds that are significantly longer with a distinctive point.

The new rose produces mature stems that are predominantly green, whereas Micaela produces mature stems with a distinctive dark red pigmentation.

2

Whereas the new cultivar bears prickles that are almost straight with a slight downward hook, Micaela bears prickles that are hooked downward at a significantly sharper angle.

This new rose cultivar originated from a pollen parent which was an undisseminated seedling of Queen Elizabeth×Romantica. The new cultivar may be distinguished from Queen Elizabeth, U.S. Plant Pat. No. 1,259, by the following combination of characteristics.

Whereas Queen Elizabeth bears flowers of a clear light pink coloration, the new rose bears flowers of a pink shade with significantly more orange tones yielding an overall coral coloration essentially as described and illustrated herein.

Whereas the new cultivar bears large flowers of a 4 to 5 inch diameter, Queen Elizabeth bears significantly smaller flowers of a $3\frac{1}{2}$ to 4 inch diameter.

Queen Elizabeth bears flowers with 35 to 40 petals whereas the new rose bears flowers of significantly lower petalage (25 to 35).

The new rose cultivar is classified as a hybrid tea, whereas Queen Elizabeth is classified as a hybrid grandiflora.

The new rose cultivar may be distinguished from Romantica by the following combination of characteristics.

Whereas Romantica bears flowers of a phlox pink coloration, the new rose bears flowers of a coral pink coloration essentially as described and illustrated herein.

Whereas the new rose bears flowers with 25 to 35 petals, Romantica bears flowers with significantly higher petalage (40 to 45).

The new rose is useful only as an outdoor garden variety, whereas Romantica is useful only as a forcing variety for greenhouse-grown cut roses.

Throughout this specification, color names beginning with a small letter signify that the name of that color, as used in common speech, is aptly descriptive. Color names beginning with a capital letter designate values based upon the R.H.S. Colour Chart published by the Royal Horticultural Society of London, England.

FLOWER

The new variety usually bears its flowers singly but sometimes two or more blooms are carried on one stem, in irregular rounded clusters. The stems are strong and of medium to long length. The plant blooms abundantly outdoors, and nearly continuously during the growing season. It has a slight tea fragrance.

BUD

The peduncle is average in length and caliper, being erect, stiff and moderately smooth, with some stipitate glands and a few small prickles.

Before the calyx breaks, the bud is medium in size, medium to long in length and pointed and ovoid in form with a few foliaceous appendages and a few stipitate glands on the surface of the bud. Usually, slender foliaceous parts extend beyond the tip of the bud equal to one-fourth or more of its length.

As the calyx breaks, the color is between Orange-Red, 35B and Red, 39B. The inner surface of the sepals carry a fine, wooly tomentum. Margins of the sepals are lined with hairs.

As the first petal opens, the bud is of average size and long, pointed and urn-shaped in form. The outside basal attachment zone of the petal is near Yellow, 4C and suffuses quickly to between Red, 38D and Red, 48D. The inside basal attachment zone of the petal is near Yellow, 6C and suffuses quickly to between Red, 43C and Red, 39B. The bud opens up well, and is not retarded or prevented from opening by cold, hot, wet or dry weather.

BLOOM

When fully open, the bloom is of average to large size, ranging from 4 to 5 inches. The petalage is double, with from 25 to 35 petals, plus from 3 to 8 petaloids arranged regularly. The bloom is very high centered to globular at first, becoming open. At first the petals are somewhat tightly cupped, with tips reflexed outward, and become later at maturity loosely cupped, with tips reflexed outward.

The petals are thick, with inside slightly shiny and outside slightly satiny. The outside and intermediate petals are broadly ovate; the outside petals have a flat apex and the intermediate petals have a rounded apex. The inside petals are round to broadly ovate in shape and have a rounded apex—sometimes with 1 or 2 notches. The colors may be modified by being bordered, shaded and/or washed or tinted with other colors.

The description immediately following is of a newly opened flower of a plant grown outdoors in the month of June in Ontario, Calif.

The basal attachment zone of the outer surface of the outside, intermediate and inside petals is near Yellow, 4C and quickly suffuses to between Red, 48B and Red, 39D. The basal attachment zone of the inner surface of all petals is near Yellow, 4B and quickly suffuses to between Red, 43D and Red, 39D. The inside surface of the outside petals sometimes had a deeper shading between Red, 39B and Red, 48B near the petal edge; there is less evidence of this deeper shading on the intermediate petals and no deeper shading on the inside surface of the inner petals.

The description which follows was made from a rose that was open for three days. It had been grown outdoors in the month of June, at Ontario, Calif.

The basal attachment zone on the outer surface of the outside and inside petals is near Yellow, 10D and quickly suffuses to between Red, 48D and Red, 54D. The basal attachment zone of the inner surface of the outside and inside petals is near Yellow, 4D and quickly suffuses to between Red, 48D and Red, 49D.

The general color effect of the newly opened flower is between Red, 43D and Red, 39D and with some blushing between Red, 49B and Red, 39B. The bloom after being three days open, gives a general color effect of between Red, 48D and Red, 49D. The petals drop off cleanly. The variety is not particularly affected by cold, hot, wet or dry weather.

The flower on the bush in the garden persists from three to four days in the month of June. Cut roses grown outdoors and kept at living-room temperatures will last from four to five days in the month of June.

REPRODUCTIVE ORGANS

There is an average number of stamens arranged irregularly about the pistils and a few are mixed with petaloids.

Filaments are of short to medium-length. Most are with anthers.

The anthers are of small to medium size and open at various times; the color when immature is near Yellow, 4D and when mature, is near Brown, 200B.

Pollen is sparse and near Yellow, 4C in color.

There is an average number (approximately 70) of pistils.

The styles are uneven, of short to average length, thin caliper, and somewhat bunched.

The stigma is near Yellow, 4A in color.

Most of the ovaries are enclosed in the calyx.

The hips are long and ovoid in form, have a conspicuous neck and are very smooth; when immature, they are near Yellow-Green, 144B in color.

The sepals are permanent, of medium-length, and spear-shaped. The color on the inside is near Yellow-Green, 145C. The outside is near Yellow-Green, 145B in color.

There is an average number to many (20 to 25) large seeds.

FOLIAGE

The compound leaves usually comprise from three to five leaflets. They are of normal to abundant quantity, medium to large in size, heavy to somewhat leathery and semi-glossy in texture. The leaflets are oval, with acute apex, and a round base. The margin is doubly serrate.

The upper surface of the mature foliage is between Yellow-Green, 147A and Green, 139A in color. The under surface is a color between Green, 138B and Greyed-Green, 191B.

The young foliage has an upper surface which is between Greyed-Purple, 187A and Red-Purple, 59A in color. The under surface is between Greyed-Purple, 183A and Greyed-Purple, 187B.

The rachis is average to heavy in size, the upper side being grooved with a few stipitate glands on the edges. The underside is sparsely prickly and with stipitate glands.

The stipules are of medium length and width and have medium-length points turning out at an angle of more than 45°.

The plant displays a more than average resistance to mildew and blackspot when compared to other varieties grown under comparable conditions in the same locality.

GROWTH

The plant is of bushy, upright to spreading habit, and much branched. It displays a very vigorous growth. The canes are of medium caliper.

The main stems are near Yellow-Green, 144B in color. They bear several large prickles which are of medium length, almost straight but hooked slightly downward, with a medium-length, broad base. The color is near Greyed-Orange, 175D. There are no small prickles and no hairs.

The branches are between Yellow-Green, 146A and Green, 137B in color. They bear several large prickles of medium length, almost straight but hooked slightly downward, with a medium-length, broad base. The color is near Yellow-Green, 151A. There are a few small prickles near Yellow-Green, 151A in color and no hairs.

New shoots have a color between Greyed-Purple, 187B and Greyed-Purple, 183A. There are several large prickles which are of medium length, almost straight but hooked slightly downward, with a medium-length, broad base. The color is near Greyed-Purple, 183A. There are several small prickles near Greyed-Purple, 183A in color and no hairs.

I claim:

1. A new and distinct variety of rose plant of the hybrid tea class, substantially as herein shown and described, being particularly characterized in its long pointed buds that open slowly with a distinctively classical spiral form; its flowers are borne mostly one-to-a-stem on long strong stems which are suitable for cutting; its extremely long vase-life as a cut rose; its unique warm orange-pink coloration that holds well throughout the life of the flower; its extremely vigorous bush is easy-to-grow and produces a profusion of flowers nearly continually throughout the growing season, making a very attractive garden specimen; its consistently fine performance in a wide variety of climatic conditions; and its abundant deep green foliage attractively clothes the entire plant.

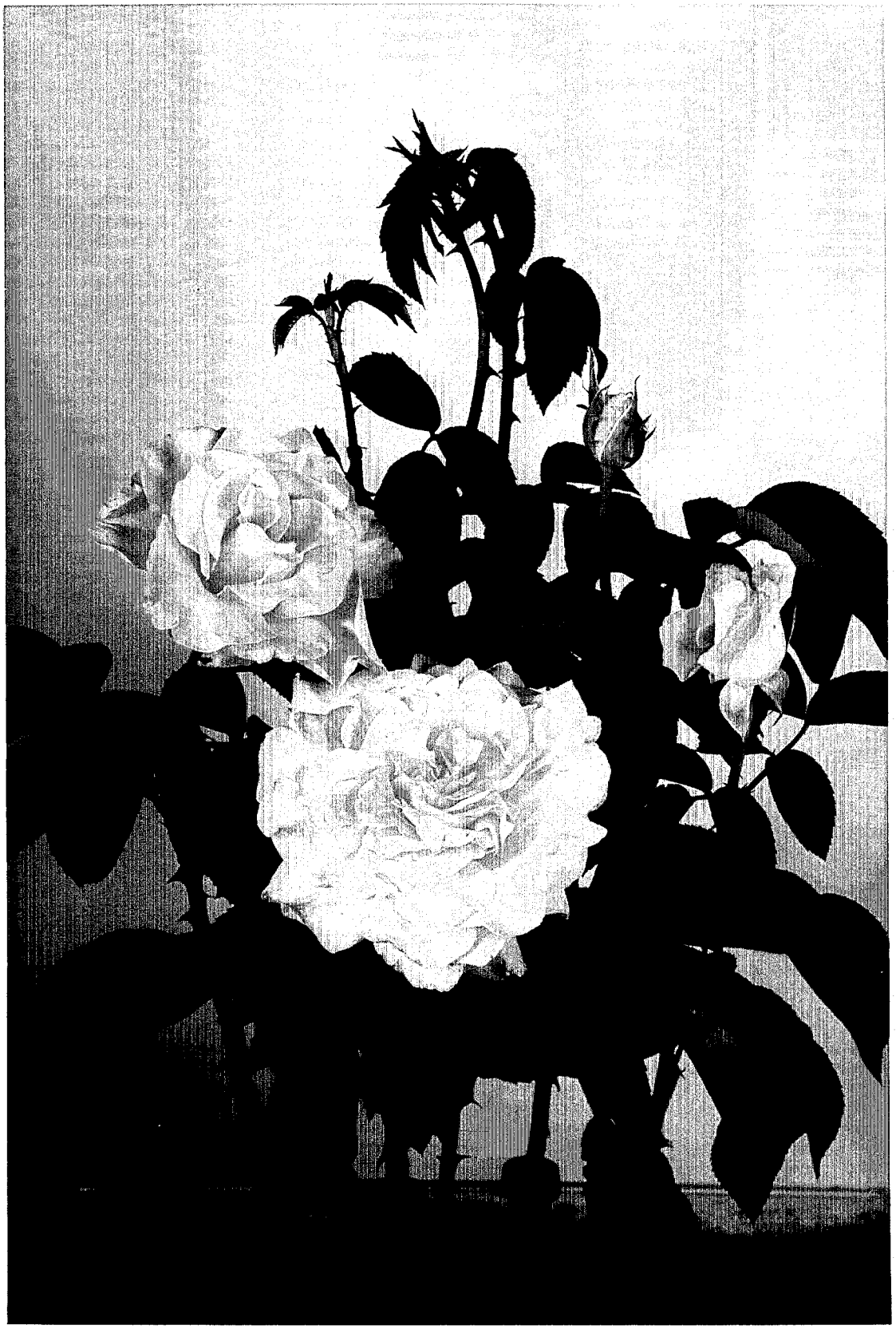

* * * * *